US007838727B2

(12) United States Patent
Lanza et al.

(10) Patent No.: US 7,838,727 B2
(45) Date of Patent: Nov. 23, 2010

(54) DERIVATION OF EMBRYONIC STEM CELLS

(75) Inventors: Robert Lanza, Clinton, MA (US); Young Chung, Shrewsbury, MA (US); Michael D. West, Mill Valley, CA (US)

(73) Assignee: Advanced Cell Technology, Inc., Marlborough, MA (US)

( * ) Notice: Subject to any disclaimer, the term of this patent is extended or adjusted under 35 U.S.C. 154(b) by 145 days.

(21) Appl. No.: 11/267,555

(22) Filed: Nov. 4, 2005

(65) Prior Publication Data
US 2006/0206953 A1 Sep. 14, 2006

Related U.S. Application Data

(60) Provisional application No. 60/726,775, filed on Oct. 14, 2005, provisional application No. 60/723,066, filed on Oct. 3, 2005, provisional application No. 60/687,158, filed on Jun. 3, 2005, provisional application No. 60/662,489, filed on Mar. 15, 2005, provisional application No. 60/624,827, filed on Nov. 4, 2004.

(51) Int. Cl.
*C12N 5/06* (2006.01)
*C12N 5/08* (2006.01)
*A61K 35/14* (2006.01)

(52) U.S. Cl. .................. 800/21; 435/366; 435/325
(58) Field of Classification Search ............... 800/21; 435/366, 325
See application file for complete search history.

(56) References Cited

U.S. PATENT DOCUMENTS

| 2002/0022268 A1 | 2/2002 | Xu et al. |
| 2002/0035735 A1* | 3/2002 | Schatten et al. ............... 800/14 |
| 2003/0087859 A1 | 5/2003 | Kochanek et al. |
| 2004/0199935 A1 | 10/2004 | Chapman |
| 2004/0229350 A1* | 11/2004 | Strelchenko et al. ........ 435/366 |
| 2005/0118713 A1 | 6/2005 | Strelchenko et al. |
| 2005/0138680 A1 | 6/2005 | Lee et al. |
| 2005/0265976 A1 | 12/2005 | Cibelli et al. |
| 2006/0014278 A1* | 1/2006 | Khillan ...................... 435/366 |
| 2006/0206953 A1 | 9/2006 | Lanza et al. |
| 2007/0298496 A1 | 12/2007 | Kuo |
| 2008/0057041 A1* | 3/2008 | Chung et al. ............... 424/93.7 |

FOREIGN PATENT DOCUMENTS

| WO | WO 95/17500 | * 6/1995 |
| WO | WO-01/50848 | 7/2001 |
| WO | WO-03/018760 | 3/2003 |
| WO | WO-2005/070011 | 8/2005 |
| WO | WO-2006/013519 | 2/2006 |
| WO | WO-2006/013573 | 2/2006 |
| WO | WO 2006/052646 | 5/2006 |
| WO | WO-2006/080952 | 8/2006 |
| WO | WO-2007/130664 | 11/2007 |

OTHER PUBLICATIONS

Rani et al., A Simple and Convenient Method for Preparing Chimeric Animals from Embryonic stem (ES) Cells Transgenic Research 2003, 739-741.*
Wilson et al., Biopsy of preimplantation mouse embryos: development of micromanipulated embryos and proliferation of single blastomeres in vitro.Biol Reprod. Jan. 1989;40(1):145-52.*
Papioannou (In Joyner, A L 2nd ed. Gene. Targeting A practical Approach, Oxford University Press, pp. 107-146.*
Van de Velde H et al., Embryo implantation after biopsy of one or two cells from cleavage-stage embryos with a view to preimplantation genetic diagnosis. Prenat Diagn. Dec. 2000;20(13):1030-7.*
Geber S et al., Blastomere development after embryo biopsy: a new model to predict embryo development and to select for transfer. Hum Reprod. Mar. 1999;14(3):782-6.*
Stem Cell: Scientific Progress and Future Research Directions. Department of Health and Human Services. Jun. 2001. </info/scireport/2001report>. Chapter 1: The Stem Cell, pp. 1-4.*
Senger. Pathways to Pregnancy and Parturition. Current Concepts, Inc.:Pullman, 1997. Chapter13, p. 221.*
Evans et al., "Establishment in culture of pluripotential cells from mouse embryos," *Nature*, 292:154-156 (1981).
Thomson et al., "Embryonic stem cell lines derived from human blastocysts," *Science*, 282:1145-1147 (1998).
Cowan et al., "Derivation of embryonic stem-cell lines from human blastocysts," *N. Engl. J. Med.*, 350:1353-1356 (2004).
Klimanskaya et al., "Derivation of human embryonic stem cells from single blastomeres," Nature Protocols,2:8: 1963-1972 (2007).
Klimanskaya et al., "Human embryonic stem cell lines derived from single blastomeres" Nature, doi:10.1038/nature05142 (2006).
Sills et al. "Identification and isolation of embryonic stem cells in reproductive endocrinology: theoretical protocols for conservation of human embryos derived from in vitro fertilization," Theoretical Biology and Meidcal Modelling. 2005,2:25, pp. 1-8.
Becker, S., et al., "Embryonic Stem Cells From Single Blastomeres," Methods Enzymol., 418:108-116 (2006).
Chung, Y., et al., "Embryonic and Extraembryonic Stem Cell Lines Derived From Single Mouse Blastomeres," Nature, 439(7073):216-219 (2006).
Delhaise, F., et al., "Establishment of an Embryonic Stem Cell Line from 8-Cell Stage Mouse Embryos," European Journal of Morphology, 34(4):237-243 (1996).
Geber, S., et al., "Proliferation of Blastomeres from Biopsied Cleavage Stage Human Embryos in Vitro: an Alternative to Blastocyst Biopsy for Preimplantation Diagnosis," Human Reproduction, 10(6):1492-1496 (1995).
Klimanskaya, I., et al., "Humeri Embryonic Stem Cell Lines Derived From Single Blastomeres" Nature, 444:481-485 (2006).

(Continued)

*Primary Examiner*—Thaian N Ton
*Assistant Examiner*—Marcia S Noble
(74) *Attorney, Agent, or Firm*—Hunton & Williams LLP

(57) ABSTRACT

This present invention provides novel methods for deriving embryonic stem cells, those cells and cell lines, and the use of the cells for therapeutic and research purposes without the destruction of the embryo. It also relates to novel methods of establishing and storing an autologous stem cell line prior to implantation of an embryo, e.g., in conjunction with reproductive therapies such as IVF.

25 Claims, 9 Drawing Sheets

OTHER PUBLICATIONS

Mitalipov, S. M., et al., "Development Of Rhesus Monkey Demi-Embryos Created By Blastomere Separation At The 2-Cell Stage," Theriogenology, 53:397 (2000).

Supplementary European Search Report dated Aug. 6, 2008 for EP 05 81 9524.

Fong et al., Unsuccessful derivation of human embryonic stem cell lines from pairs of human blastomeres, Reprod Biomed Online. Aug. 2006;13(2):295-300.

Wade, N. "Stem Cell Test Tried on Mice Saves Embryo." New York Times, Oct. 17, 2005, available on-line at http://www.nytimes.com/2005/10/17/health/17stem.html?pagewanted=print, pp. 1-2.

Robertson, "Embryo-derived stem cells," in *Teratocarcinomas and Embryonic Stem cells* (1987) IRL Press Oxford, pp. 71-112.

Bradley, "Production and analysis of chimaeric mice," in *Teratocarcinomas and Embryonic Stem cells* (1987) IRL Press Oxford, pp. 113-151.

Schraermeyer et al., "Subretinally transplanted embryonic stem cells rescue photoreceptor cells from degeneration in the RCS rats," Cell Transplant. 2001;10(8):673-80.

Wang, et al., "Increases in phosphorylation of SAPK/JNK and p38MAPK correlate negatively with mouse embryo development after culture in different media," Fertil Steril. Apr. 2005;83 Suppl 1:1144-54.

Chesne, et al., "Nuclear transfer in cattle: birth of cloned calves and estimation of blastomere totipotency in morulae used as a source of nuclei," C R Acad Sci III. 1993;316(5):487-91.

Supplementary European Search Report received in EP 07 79 4602 dated Feb. 18, 2010.

Geber, Proliferation of blastomeres from biopsied cleavage stage human embryos in vitro: an alternative to blastocyst biopsy for preimplantation diagnosis, Human Reproduction, 1995, vol. 10(6), pp. 1492-1496.

Van de Velde, The four blastomeres of a 4-cell stage human embryo are able to develop individually into blastocysts with inner cell mass and trophectoderm, Human Reproduction, 2008, vol. 23:8, pp. 1742-1747.

Wakayama, Efficient Establishment of Mouse Embryonic Stem Cell Lines from Single Blastomeres and Polar Bodies, Stem Cell, 2007, vol. 25, pp. 986-993.

Solter, Immunosurgery of mouse blastocyst, Proc. Nat. Acad. Sci., Dec. 1975, vol. 72(12), pp. 5099-5102.

Schuldiner, Selective Ablation of Human Embryonic Stem Cells Expressing a "Suicide" Gene, Stem Cell, 2003, vol. 21, pp. 257-265.

Ogawa, A novel mechanism for regulating clonal propagation of mouse ES cells, Genes to Cell, 2004, vol. 9, pp. 417-477.

Harvey, Inducible control of gene expression: prospects for gene therapy, Current Opinion in Chemical Biology, 1998, vol. 2, pp. 512-518.

Springer, Prodrug-activating systems in suicide gene therapy, The Journal of Clinical Investigation, May 2000, vol. 105(9), pp. 1161-1167.

Thomson, Isolation of a primate embryonic stem cell line, Proc. Natl. Acad. Sci., Aug. 1995, vol. 92, pp. 7844-7848.

Andrews, From teratocarinomas to embryonic stem cells, Phil. Trans. R. Soc. Lond. B, 2002, vol. 357, pp. 405-417.

Ouhibi, Initial Culture Behaviour of Rat Blastocysts on Selected Feeder Cell Lines, Molecular Reproduction and Development, 1995, vol. 40, pp. 311-324.

* cited by examiner

DERIVATION OF EMBRYONIC STEM CELLS

CROSS REFERENCE TO RELATED APPLICATIONS

This application claims the benefit of United States Provisional Application Nos.: 60/624,827, filed Nov. 4, 2004; 60/662,489, filed on Mar. 15, 2005; 60/687,158, filed Jun. 3, 2005; 60/723,066, filed on Oct. 3, 2005 and 60/726,775, filed on Oct. 14, 2005. The disclosures of these applications are hereby incorporated by reference in their entirety.

FIELD OF THE INVENTION

This invention generally relates to novel methods for deriving embryonic stem cells, those cells and cell lines, and the use of the cells for therapeutic and research purposes. It also relates to novel methods of establishing and storing an autologous stem cell line prior to implantation of an embryo, e.g. in conjunction with assisted reproductive technologies such as in vitro fertilization.

BACKGROUND OF THE INVENTION

With few exceptions, embryonic stem cells have only been grown from blastocyst-stage embryos. ES cell lines are conventionally isolated from the inner cell mass of blastocysts and in a few instances from cleavage stage embryos. There are several drawbacks to the techniques used to create these cells. From the perspective of the technique, the culturing of embryos to blastocysts occasionally has a relatively low success rate. Some people express the basic objection that embryonic stem (ES) cell research is rooted in the fact that ES-cell derivation deprives preimplantation-stage embryos of any further potential to develop into a complete human being. The following invention provides novel and unexpected methods of deriving embryonic stem cell lines and other embryo-derived cells for use in research and in medicine.

BRIEF DESCRIPTION OF THE FIGURES

FIGS. 2B-2D show immunostaining for the same cells expressing both Oct-4 (2B) and Lac-Z(2C). FIG. 2D represents counterstaining with DAPI. Bar, 100 um.

In FIG. 3A shows a mouse embryo that was fixed in 2% glutaraldehyde, 4% paraformaldehyde overnight and stained for Lac-Z using a kit form Sigma. FIGS. 3B-3D show immunofluorescence staining for molecular markers of primitive endoderm (α-feto protein, 3B), ectoderm (βIII tubulin, 3C) and mesoderm (muscle actin, 3D). Bar, 100 um.

FIGS. 4A (green fluorescence) and 4B (Hoffman modulation optics) visualize an aggregate of GFP mES cells 48 hours after aggregation with single blastomeres. The arrow in FIG. 4B shows a protruding cluster of GFP-negative cells not visible in FIG. 4A. FIGS. 4C (green fluorescence) and 4D (phase contrast) demonstrate outgrowth of GFP-negative cells aggregated with GFP$^+$ mES cells, after being plated on mouse embryo fibroblast cells (MEF). The arrows in FIGS. 4C and 4D point to GFP-negative cells. FIGS. 4E (green fluorescence) and 4F (phase contrast) display growth of GFP$^+$ mES cells and cells arising from a single blastomere after mechanical dissociation of initial outgrowth. The arrows in FIGS. 4E and 4F point to remaining GFP$^+$ mES cells. FIG. 4G represents cells derived from a single blastomere grown on MEF alone for four days without ES cells, stained with Tromal, which labels trophoblast cells. FIG. 4H shows the same cells as Figure G, but are stained with DAPI to show the three nuclei. Scale bar, 100 um.

FIG. 5A provides PCR analysis using LacZ-specific primers demonstrating the presence of the LacZ gene in the ES and TS cell lines. FIG. 5B shows PCR analysis for GFP-specific primers showing the absence of helper-ES cell (GFP positive) contamination. In FIG. 5C, RT-PCR analysis reveals robust expression of the Oct-4 gene (5C) in the ES cell lines, but much lower levels in the TS cell lines. The TS cell lines showed a large PCR product in addition to the expected fragment. Figure 5D represents analysis of nanog gene demonstrating moderate to high levels of expression in the ES cell lines, and moderate levels in the TS cell lines. FIG. 5E shows similar levels of Rex-1 gene expression in ES and TS cells lines. FIG. 5F shows high levels of trophoblast marker Cdx-2 gene expression in the TS cell lines, and low to negligible levels in the ES cell lines. FIG. 5G shows α-Tubulin used as a control for the input of RNA samples. The abbreviations present in FIG. 5 are as follows: M, molecular weight marker; LacZ, genomic DNA isolated from 129/Sv-ROSA26:LacZ mouse tails; GFP, genomic DNA isolated from green fluorescent protein (GFP)-positive 129Sv/CD-1 mouse ES cells; CD-1, genomic DNA isolated from CD-1 mouse tails; H, $H_2O$ control. PL, mouse placental RNA, M, molecular weight marker; H, $H_2O$ control.

FIGS. 6A and 6B show phase contrast photos of typical colonies. FIGS. 6C and 6D represent Lac-Z stained colonies, demonstrating their single blastomere origin. FIGS. 6E and 6F show alkaline phosphatase staining. FIGS. 6G and 6H show indirect immunofluorescence with antibodies to Oct-4. FIG. 6I depicts putative ES cells stained with antibodies to SSEA-1. FIG. 6J shows TROMA-1 antibody staining of the putative TS cells (same field as FIG. 6H). Scale bar, 200 um.

FIGS. 8A-8C show immunofluorescence analysis of molecular markers of mesoderm (muscle actin, FIG. 8A), primitive endoderm (α-feto protein, FIG. 8B), and ectoderm (β III tubulin, FIG. 8C). FIG. 8D depicts representative chromosome spreads of two single blastomere-derived mES cell line. G-banded karyotyping shows that lines Y1 (top) and Y7 (bottom) have XY and XX karyotypes, respectively. FIG. 8E shows hematoxylin and eosin stained section through a teratoma and shows examples of tissue from all three germ layers. Bn, bone (mesoderm); nt, neural tissue (ectoderm); cre, ciliated respiratory epithelium (endoderm). The insert of FIG. 8E is an enlarged region of ciliated respiratory epithelium. FIG. 8F shows 11.5 day chimeric embryos produced from three of the putative ES cell lines, each of which shows the high degree of chimerism frequently observed. FIG. 8G is a closeup view of lacZ-stained chimera from putative ES line J-15. The arrow points to the placental labyrinth, which is also chimeric and is derived from extraembryonic mesoderm, not trophectoderm. FIG. 8H displays chimeric pups generated by aggregating blastomere-derived (1 29/Sv) ES cells (lines J15 and Y1) with CD-1 mouse embryos. Scale bars: A-D—200 um, F—10 mm, G—2 mm.

SUMMARY OF THE INVENTION

Figure 1:
FIG. 1 shows fibroblast-like cells originating from ES colonies that can be expanded for use as autologous feeders.

The present invention provides novel methods for deriving embryonic stem cells, those cells and cell lines, and uses of the embryonic stem cells and cell lines for therapeutic and research purposes. It also relates to a method of establishing and storing an autologous stem cell line from a blastomere retrieved prior to implantation of an embryo, e.g. in conjunction with assisted reproductive technologies such as in vitro fertilization ("IVF").

This invention provides a method of producing an embryonic stem cell, comprising the step of culturing a blastomere obtained from an embryo, wherein the embryo remains viable. In one embodiment, the blastomere is obtained from an embryo prior to compaction of the morula. In another embodiment, the embryo is obtained before formation of the blastocoel. The blastomere may be obtained by partial or complete removal of the zona pellucida surrounding the embryo. The embryo may be implanted or cryopreserved.

The blastomere obtained from the embryo is cultured with any suitable cell to produce an ES cell. Cells suitable for culturing the blastomeres include, but are not limited to, embryonic stem cells, such as from already established lines, embryo carcinoma cells, murine embryonic fibroblasts, other embryo-like cells, cells of embryonic origin or cells derived from embryos, many of which are known in the art and available from the American Type Culture Collection, Manassas, VA 20110-2209, USA, and other sources. The blastomere may also be cultured with factors that inhibit differentiation of the ES cell. In one embodiment, the blastomere is cultured in the presence of heparin. In another embodiment, Oct-4 is introduced into the blastomere or alternatively, expression of endogenous Oct-4 is induced in the blastomere.

In one embodiment, the present invention provides a method of producing an ES cell comprising the steps of obtaining a blastomere from an embryo, wherein the embryo remains viable, aggregating the blastomere with ES cells, culturing the aggregated blastomere and ES cells until the blastomere exhibits properties of ES cells, and isolating the ES cells derived from the blastomere.

In another embodiment, the blastomere obtained from an embryo is cultured with autologous feeder cells, wherein the feeder cells are produced by culturing a blastomere obtained from the same embryo under conditions to differentiate the blastomere into a somatic cell to produce the autologous feeder cells.

In a further embodiment, a blastomere obtained from an embryo undergoes cell division and one progeny cell is used for genetic testing and another progeny cell is used to produce an ES cell.

In one embodiment, the method of producing an ES cell or ES cell line comprises obtaining a blastomere through biopsy, removing the zona pellucida, separating the blastocyst into two segments, culturing one blastocyst segment in order to produce an ES cell or ES cell line and implanting or cryopreserving the remainder of the blastocyst. In another embodiment the method comprises the steps of obtaining a single blastomere prior to implantation and before formation of the blastocoel, culturing the blastomere, adding ES cells from already established lines, allowing the ES cells to clump around the blastomere until the blastomere exhibits ES cell growth and harvesting the resultant ES cell for therapeutic purposes. In yet another embodiment, the method comprises the steps of obtaining a single blastomere before compaction of the morula, culturing the blastomere in standard culture conditions, adding mitotically inactivated ES cells from already established lines until ES cells begin to form, and harvesting or cryopreserving the resultant ES cells. In a further embodiment, the method comprises the steps of obtaining a single blastomere prior to implantation and before formation of the blastocoel, culturing the blastomere, adding ES cells from already established lines, and introducing recombinant Oct-4 into the blastomere or activating endogenous Oct-4.

The ES cell produced from the blastomere may be pluripotent or totipotent. Pluripotency or totipotency of the ES cell may be determined by assaying for ES cell marker proteins. Such proteins include Oct-4, SSEA-1, nanog, alkaline phosphatase and Res-1.

The method of the invention may be performed on mammals, e.g., mice, rabbits, sheep, pigs, cows, primates and humans. In one embodiment, the mammal is a non-human mammal. In another embodiment, the mammal is a human.

The present invention also provides methods of differentiating the ES cells produced by the methods of the invention. The ES cells may be differentiated into any cell type including those of mesodermal, endodermal and ectodermal origin.

Also contemplated are methods of differentiating the blastomere obtained from an embryo into a differentiated cell type, e.g., mesoderm, endoderm or ectoderm without first producing an ES cell from the blastomere.

The invention also encompasses the ES cells produced by the methods of this invention, ES cell lines derived from these ES cells as well as differentiated cells derived from the ES cells or cell lines.

The ES cells provided by this invention or cells derived from the ES cells are useful for treating disorders amenable to cell therapy. Pharmaceutical compositions comprising these cells together with a pharmaceutically acceptable medium or carrier are also provided.

Also provided are methods of producing trophoblast stem (TS) cells comprising the step of culturing a blastomere obtained from an embryo, wherein the embryo remains viable. In one embodiment, blastomere is obtained prior to compaction of the morula. In another embodiment, the blastomere is obtained before formation of the blastocoel. The blastomere may be obtained by partial or complete removal of the zona pellucida surrounding the embryo.

The blastomere obtained from the embryo is cultured with any suitable cell to produce a TS cell. Cells suitable for culturing the blastomeres include, but are not limited to, embryonic stem cells, such as from already established lines, embryo carcinoma cells, murine embryonic fibroblasts, other embryo-like cells, cells of embryonic origin or cells derived from embryos, many of which are known in the art and available from the American Type Culture Collection, Manassas, VA 20110-2209, USA, and other sources. The blastomere may also be cultured with factors that induce differentiation of the ES cell. In one embodiment, the blastomere is cultured in the presence of FGF-4.

The TS cell produced by the methods of the invention may express a TS cell marker, e.g., nanog, Rex-1, cdx-2. The TS cell may also lack expression of Oct-4 or α-fetoprotein. The TS cell may also be cultured to produce a TS cell line or differentiated.

DETAILED DESCRIPTION OF THE INVENTION

The present invention is based in part on the discovery that stem cells can be generated from embryos without affecting viability of the embryo. In one embodiment, these methods utilize in vitro techniques currently used in pre-implantation genetic diagnosis (PGD). As demonstrated herein, pluripotent embryonic stem (ES) cell lines can be generated from a single blastomere removed from an embryo without interfering with the embryo's normal development to birth.

Removal of the Blastomere

The blastomere may be removed from an embryo at various developmental stages prior to implantation including but not limited to: before compaction of the morula, during compaction of the morula, before formation of the blastocoel or during the blastocyst stage.

In one embodiment the invention provides methods for biopsy of a blastocyst which will produce embryonic stem cells, and the remainder of the blastocyst is implanted and results in a pregnancy and later in a live birth. In an example of this: the zona pellucida is removed from the blastocyst by any means known to those of ordinary skill in the art (in this instance using acidic tyrode solution pH 2.4), it is placed on culture ware with protein free media (CZB protein free media pH 7.4 is used, but other protein free media could be used) and it adheres, then the blastocyst is biopsied. This was done using a small segment of razor blade attached to a pipette, and it was cut once separating the blastocyst into two segments—preferably less than 30%, 20%, 10% or 5% of the blastocyst is biopsied. Serum is then added to the media to dissociate the blastocyst and the biopsied segment is used to derive embryonic stem cells or other embryo-derived cells through means well known to those of ordinary skill in the art (e.g., allowing the biopsy to grow on embryonic fibroblasts, on feeder-free matrix, etc.) while the remainder of the blastocyst is implanted or cryopreserved.

In another embodiment the controversies associated with the derivation of embryonic stem cells are circumvented by using a technique similar to that used in preimplantation genetic diagnosis (PGD) where a single blastomere is removed from the embryo, preferably before the compaction of the morula. These methods can be adapted for use in the present invention, for the removal of one or more cells from an embryo without affecting the continued development of the embryo. In one embodiment, the biopsied blastomere is allowed to undergo cell division and one progeny cell is used for genetic testing and the remaining cells are used to generate stem cells. The biopsied embryo may be implanted at the blastocyst stage or frozen for implantation at a later time.

The biopsy consists of two stages. The first is to make a hole in, or in some instances fully remove, the zone pellucida that surrounds the embryo. Once the hole is made, the cells (preferably one or two) may then be removed from the embryo. In certain preferred embodiments, the method involves removing or generating an extraction hole in the zona pellucida, and can be carried out by one more techniques selected from the group consisting of physical manipulation, chemical treatment and enzymatic digestion. Exemplary techniques that can be used include:

Partial zone dissection (PZD:): partial dissection of the zona pellucida, using a micro-pipette;

Zona drilling: chemical opening of the zona pellucida zone through partial digestion with Tyrode acid;

Zona drilling: enzymatic opening of the zona pellucida zone through partial digestion with pronase or other protease;

zona pellucida thinning: thinning of the zona pellucida with Tyrode acid or laser;

Point-like opening of the zona pellucida with laser;

Point-like mechanical opening of the zona pellucida with Piezo micro-manipulator.

To briefly illustrate one embodiment, the procedure is performed on day 3 of embryo development, when the embryo is around 6-8 cell stage. The embryo is placed in a drop of biopsy medium under mineral oil by holding it with a holding pipette. The zona pellucida is locally digested, by releasing acidified Tyrode's solution (Sigma, St. Louis, Mo. 63178) through an assistant hatching pipette. Once the hole is made, cells (blastomeres) can be aspirated through the hole.

To illustrate another embodiment, the zona pellucida of the blastocyst may be at least partially digested by treatment with one or more enzymes or mixture of enzymes such as pronase. A brief pronase (Sigma) treatment of blastocysts with an intact zona pellucida results in the removal of the zona. Other types of proteases with the same or similar protease activity as pronase may also be used.

Culturing the Blastomere

The isolated blastomeres may be cultured by placing them on cultureware (e.g., in microwells) with media in standard culture conditions together with any suitable cells including but not limited to embryonic stem cells, such as from already established lines, embryo carcinoma cells, murine embryonic fibroblasts, other embryo-like cells, cells of embryonic origin or cells derived from embryos, many of which are known in the art and available from the American Type Culture Collection, Manassas, VA 20110-2209, USA, and other sources. These cells clump or aggregate around the blastomere. Other methods of aggregation including methods using microwell microbeads or the hanging drop method, or any other aggregation method known in the art may be used. While not wishing to be bound by any particular theory, it is believed that over a period of days or weeks the cultured blastomeres exhibit ES cell growth perhaps as a result of cell-cell interactions between the blastomeres and the co-cultured embryonic cells or from interactions between the blastomeres and factors secreted by the embryonic cells.

The blastomere(s) may be co-cultured with the remaining embryo. In one embodiment, the blastomeres are co-cultured with the remaining embryo in a microdroplet culture system or other culture system known in the art, which permits cell-cell, cell-secreted factor and/or cell-matrix contact. The volume of the microdrop may be reduced, e.g., from 50 microliters to about 5 microliters to intensify the signal and promote cell-cell interactions.

In certain embodiments, the blastomere culture conditions may include contacting the cells with factors that can inhibit or otherwise potentiate the differentiation of the cells, e.g., prevent the differentiation of the cells into non-ES cells, trophectoderm or other cell types. Such conditions can include contacting the cultured cells with heparin or introducing Oct-4 into the cells (such as by including Oct-4 in the media) or activating endogenous Oct-4 in the cells.

Autologous Feeder Cells

The present invention also provides a method of plating early pre-blastocyst embryos to make stem cells on autologous feeder cells. In one embodiment, this method comprises (a) splitting a pre-blastocyst embryo, (b) plating one part into tissue culture under conditions to directly differentiate it into somatic cells to make feeder cells and (c) plating the other part of the pre-blastocyst embryo on the autologous feeder cells. In another embodiment, the autologous feeder cells and ES cells are produced from blastomeres removed from the pre-blastocyst embryo, thus, preserving the ability of the embryo to be implanted.

Pluripotency of ES Cells

Pluripotency of the ES cells produced by the methods of this invention can be determined by detecting expression of ES cell marker proteins. Examples of such proteins include but are not limited to octamer binding protein 4 (Oct-4), stage-specific embryonic antigen (SSEA)-1, nanog, alkaline phosphatase and Rex-1. In some embodiments, the putative ES cell lines maintain pluripotency after more than 13, 20, 30, 40, 50, 60, 70, 80, 90 or 100 passages. The ES cells may also be assayed for maintenance of normal karyotype.

Production of TS Cells

This invention also provides methods of producing trophoblast stem ("TS" cells) by contacting blastomere outgrowths, which morphologically resemble trophoblast and/or extraembryonic endoderm, but which do not resemble ES cells, with FGF-4. For example, FGF-4 is added to the culture media of the outgrowths. TS cells can be detected by assaying expression of proteins such as nanog, Rex-1, and Cdx-2, using procedures standard in the art. TS cell identification can also be evidenced by absence of the expression of proteins such as, but not limited to Oct-4 and α-feto protein.

Therapeutic Uses of ES Cells

The present invention provides a method of treating a disorder amendable to cell therapy comprising administering to the affected subject a therapeutically effective amount of the ES cells of the invention. The ES cells of this invention are suitable for any use that ES cells are useful.

In one embodiment the methods of the invention are used to remove a blastomere preceding implantation of an embryo after which the blastomere would be cultured as described above in order to derive and store embryonic stem cells for therapeutic uses using cell therapy should the child resulting from the embryo require, for example, disease therapy, tissue repair, transplantation, treatment of a cellular debilitation, or treatment of cellular dysfunctions in the future.

In another embodiment of the invention, cells derived from a blastomere, precompaction morula, compacting morula, or sectioned blastocyst are directly differentiated in vitro or in vivo to generate differentiating or differentiated cells without generating an embryonic stem cell line. These embryo-derived cells, like embryonic stem cells are useful in medical and biological research and in the treatment of disease by providing cells for use in cell therapy, e.g., allogeneic cell therapy.

The embryonic stem cells and embryo-derived cells generated by the above-mentioned novel techniques are utilized in research relating to cell biology, drug discovery, and in cell therapy, including but not limited to production of hematopoietic and hemangioblastic cells for the treatment of blood disorders, vascular disorders, heart disease, cancer, and wound healing, pancreatic beta cells useful in the treatment of diabetes, retinal cells such as neural cells and retinal pigment epithelial cells useful in the treatment of retinal disease such as retinitis pigmentosa and macular degeneration, neurons useful in treating Parkinson's disease, Alzheimer's disease, chronic pain, stroke, psychiatric disorders, and spinal cord injury, heart muscle cells useful in treating heart disease such as heart failure, skin cells useful in treating wounds for scarless wound repair, burns, promoting wound repair, and in treating skin aging, liver cells for the treatment of liver disease such as cirrhotic liver disease, kidney cells for the treatment of kidney disease such as renal failure, cartilage for the treatment of arthritis, lung cells for the treatment of lung disease and bone cells useful in the treatment of bone disorders such as osteoporosis.

Such cell therapy methods may involve use of the ES cells of this invention in combination with proliferation factors, lineage-commitment factors, or gene or proteins of interest. Treatment methods may include providing stem or appropriate precursor cells directly for transplantation where the tissue is regenerated in vivo or recreating the desired tissue in vitro and then providing the tissue to the affected subject.

Unless otherwise defined, all technical and scientific terms used herein have the same meaning as commonly understood by one of ordinary skill in the art. In case of conflict, the present specification, including definitions, will control. Further, unless otherwise required by context, singular terms shall include pluralities and plural terms shall include the singular. Generally, nomenclatures used in connection with, and techniques of, cell and tissue culture, molecular biology, immunology, microbiology, genetics, developmental biology, cell biology described herein are those well-known and commonly used in the art. Exemplary methods and materials are described below, although methods and materials similar or equivalent to those described herein can also be used in the practice or testing of the present invention.

All publications and other references mentioned herein are incorporated by reference in their entirety. Although a number of documents are cited herein, this citation does not constitute an admission that any of these documents forms part of the common general knowledge in the art. Throughout this specification and claims, the word "comprise," or variations such as "comprises" or "comprising" will be understood to imply the inclusion of a stated integer or group of integers but not the exclusion of any other integer or group of integers.

In order for that this invention may be better understood, the following examples are set forth. These examples are for purposes of illustration only and are not be construed as limiting the scope of the invention in any matter.

EXAMPLE 1

Generation of ES Cell Lines

Figure 4:
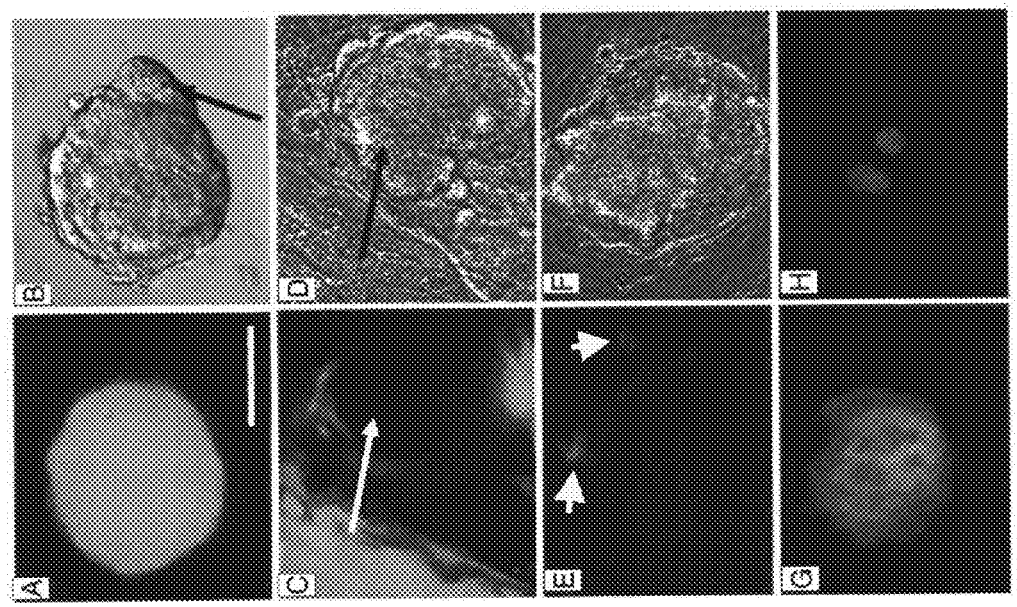
FIG. 4 illustrates stages of single blastomere growth in the presence (4A-4F) or absence (4G, 4H) of mES cells.

Single blastomeres were isolated from 8-cell stage 129/Sv-ROSA26:LacZ mouse embryos either by biopsy through a hole in the zona pellucida drilled using Piezo-pulse or by disaggregating of zona-denuded embryos in Ca++/Mg++ free PBS for 10 minutes. The biopsied (7-cell) embryos were transferred to the oviducts of 1.5 days post coitum (d.p.c.) synchronized surrogate mothers, and each separated blastomere aggregated with a small clump (approximately 100 cells) of green fluorescent protein (GFP)-positive 129Sv/CD-1 mouse ES (mES) cells in a 300 um depression created by pressing an aggregation needle into the bottom of a plastic tissue culture plate. After incubation for 24-48h a growing "bud" of GFP-negative cells was observed on the sides of the majority (60%) of GFP-mES clusters (See FIG. 4 A, B). The cell clumps were plated onto mitomicin C-treated mouse embryonic fibroblasts (MEF) and cultured in knockout DMEM (15% FCS, penicillin/streptomycin, Glutamax-I, β-mercaptoethanol, nonessential amino acids, LIF [2000U/ml], and MEK1 inhibitor [50 µM] (mES culture medium)). See, for example, Hogan et al. *Manipulating the Mouse Embryos: A Laboratory Manual*. Cold Spring Harbor Laboratory Press; 2nd Edition, 1994. The majority of blastomeres (54/91) formed rapidly growing clumps of cells within 4 days, which were separated from GFP-positive mES cells under a fluorescence microscope. The cells were expanded by mechanical dissociation or trypsinization, while selecting for the colonies morphologically resembling ES cells and excluding any GFP-positive cells (FIG. 4, C, D, E, F).

Figure 2:
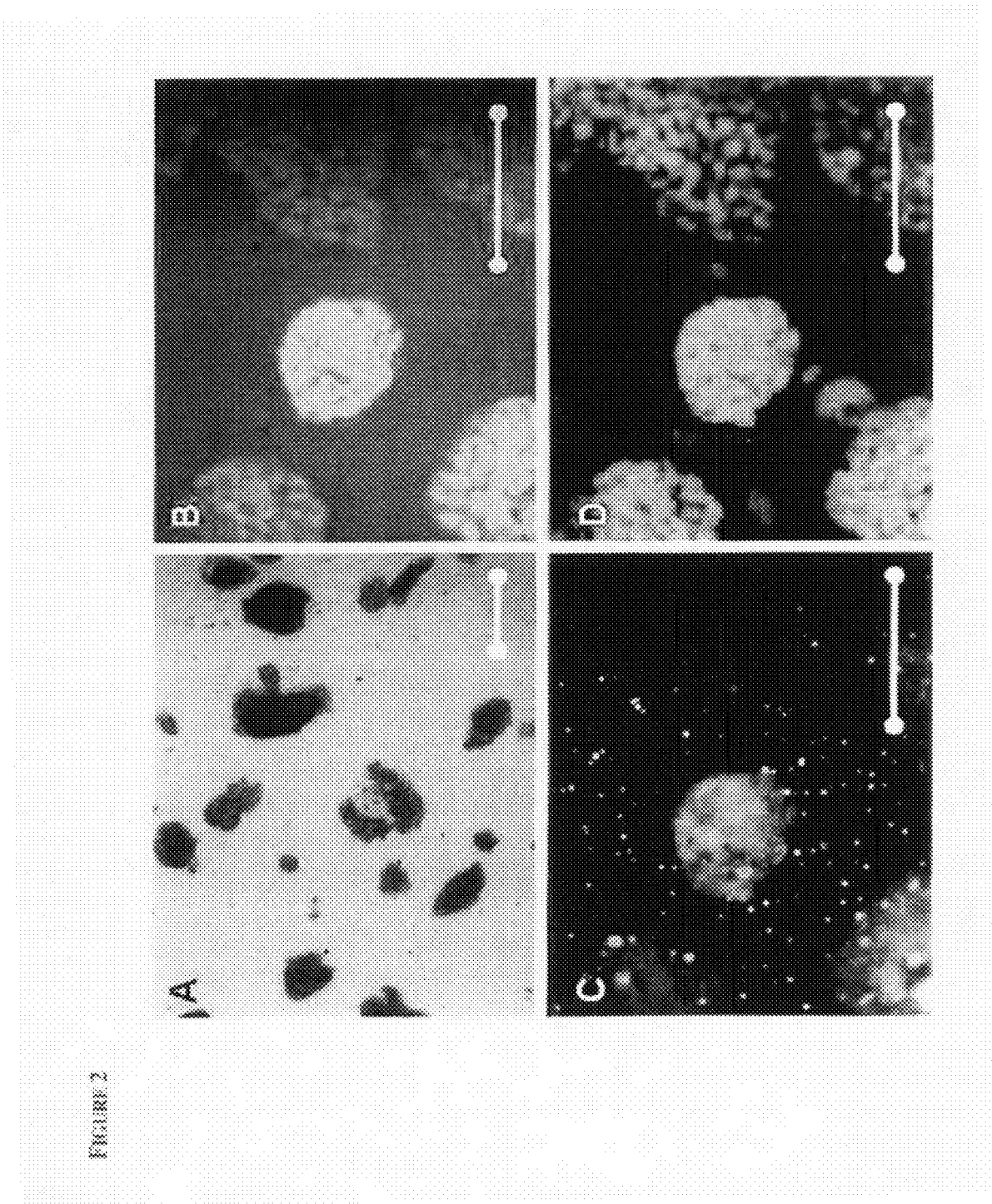
FIG. 2 depicts blastomere-derived mES cells stained for Lac-Z using a kit from Sigma (A).
Figure 6:
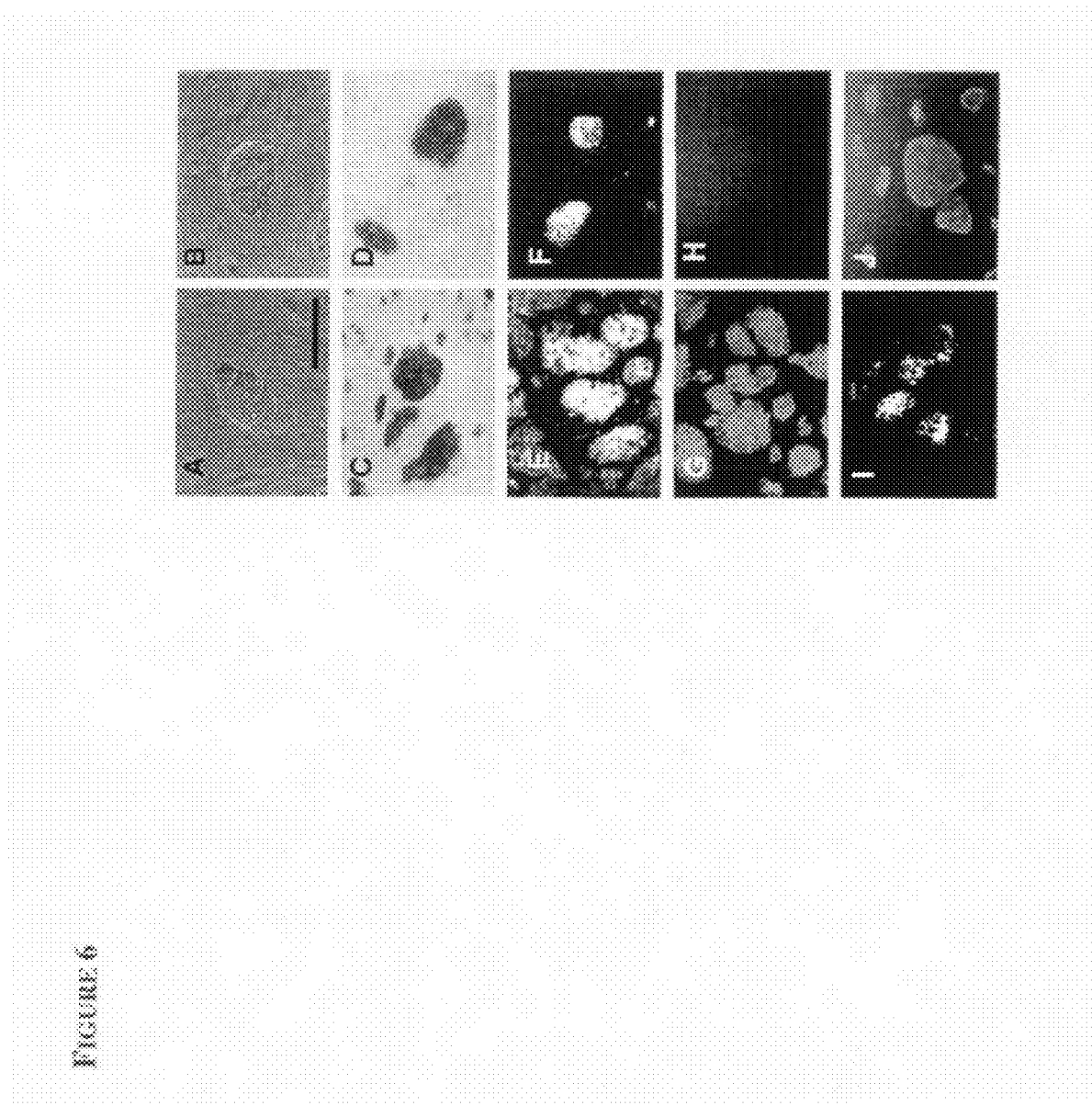
FIG. 6 illustrates a comparison of putative ES (left column) and TS (right column) cell lines derived from single blastomeres.

Several lines of LacZ positive ES-like cells were produced (Table 1, FIG. 6 C) which maintained normal karyotype (FIG. 8 D) and markers of pluripotency after over 50 passages. Each line expressed octamer binding protein 4 (Oct-4), stage-specific embryonic antigen (SSEA)-1, nanog, and alkaline phosphatase (FIG. 2 and FIG. 6 E,G,I). Indirect immunofluorescence staining for ES cell protein markers was performed on cells growing on 4-well tissue culture plates. For example, see Lanza R, et al, Eds. *Handbook of stem Cells. Vol 1:Embryonic Stem Cells* (Elsevier/Academic Press, San Diego, Calif., 2004); Evans, M. J.,. Kaufman, M. H., Nature 292, 154 (1981); Thomson JA et al., 282, 1145 (1998); Cowan C. A. et al., N. Engl J Med. 350, 1353 (2004). The following primary antibodies were used: Oct-4 (Santa Cruz Biotechnology, Santa Cruz, Calif.), SSEA-1 (developed by Solter and Knowles and obtained through the DSHB of the University of Iowa, Iowa City, Iowa), Troma-1 (raised by Brulet and Kemler and obtained through DSHB), α-feto protein (DACO), βIII tubulin (Covance, Berkeley, Calif.) and muscle actin (Abcam, Cambridge, Mass.). Alkaline phosphatase staining was performed using the Vector Red kit from Vector Laboratories.

Polymerase chain reaction (PCR) analysis revealed the presence of LacZ but not GFP gene sequences in these cells (FIG. 5 A, B), confirming that the lines originated from the blastomeres and not the ES cells used for aggregation. Briefly, genomic DNA was isolated from ES and TS cells using a QIAamp DNA Mini Kit (Qiagen, Valencia, Calif.), and 100 ng per reaction was used for both GFP and LacZ gene amplification. We used forward (5'-TTGAATTCGCCACCATGGTGAGC-3') (SEQ ID NO:1) and reverse (5'-TTGAATTCTTACTTGTACAGCTCGTCC-3') (SEQ ID NO:2) primers for GFP gene with reaction parameters of 95° C. for 9 min (1 cycle) and 94° C. for 45 s, 59° C. for 1 min, 72° C. for 1.5 min for 37 cycles. PCR products were separated on 1.5% agarose gel and visualized by ethidium bromide staining. LacZ gene genotype analysis was performed with primers and PCR parameters recommended by The Jackson Laboratory (Bar Harbor, Me.).

In two control experiments, individual blastomeres (n=44) isolated from 8-cell embryos were plated into 20-100 µl drops containing mES cell culture medium. The majority of the blastomeres failed to divide over the 10 day period of culture, whereas 9 (20%) generated small clusters of differentiated trophoblast-like giant cells (FIG. 4 G, H) before arresting at the 2- to-6 cell stage. This suggests that cell co-culture or the exposure of the blastomeres to substances secreted by the ES cells may be critical to the success of this method.

EXAMPLE 2

Differentiation of ES Cells

Figure 3:
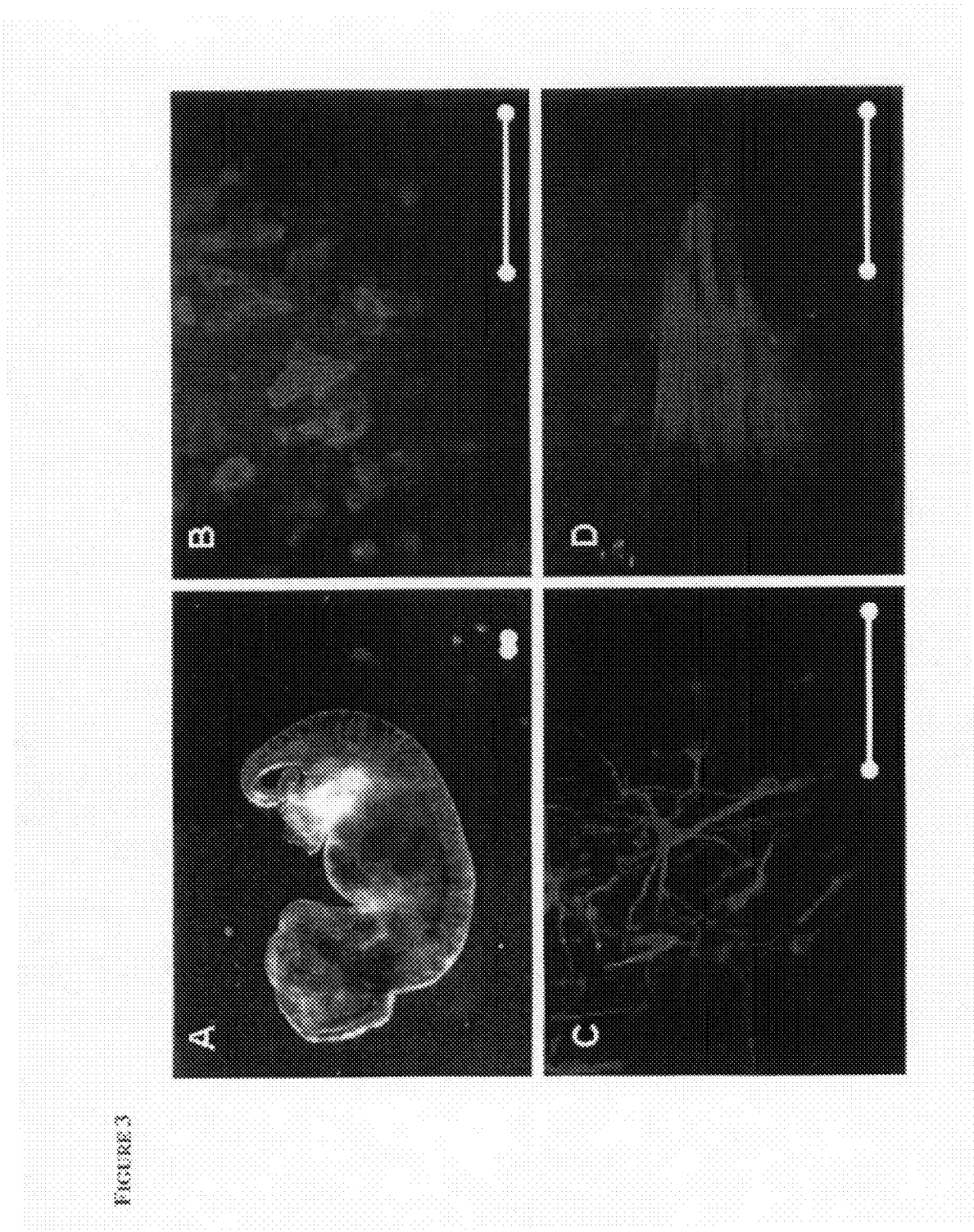
FIG. 3 shows differentiation of blastomere-derived mES cells in vivo and in vitro.
Figure 8:
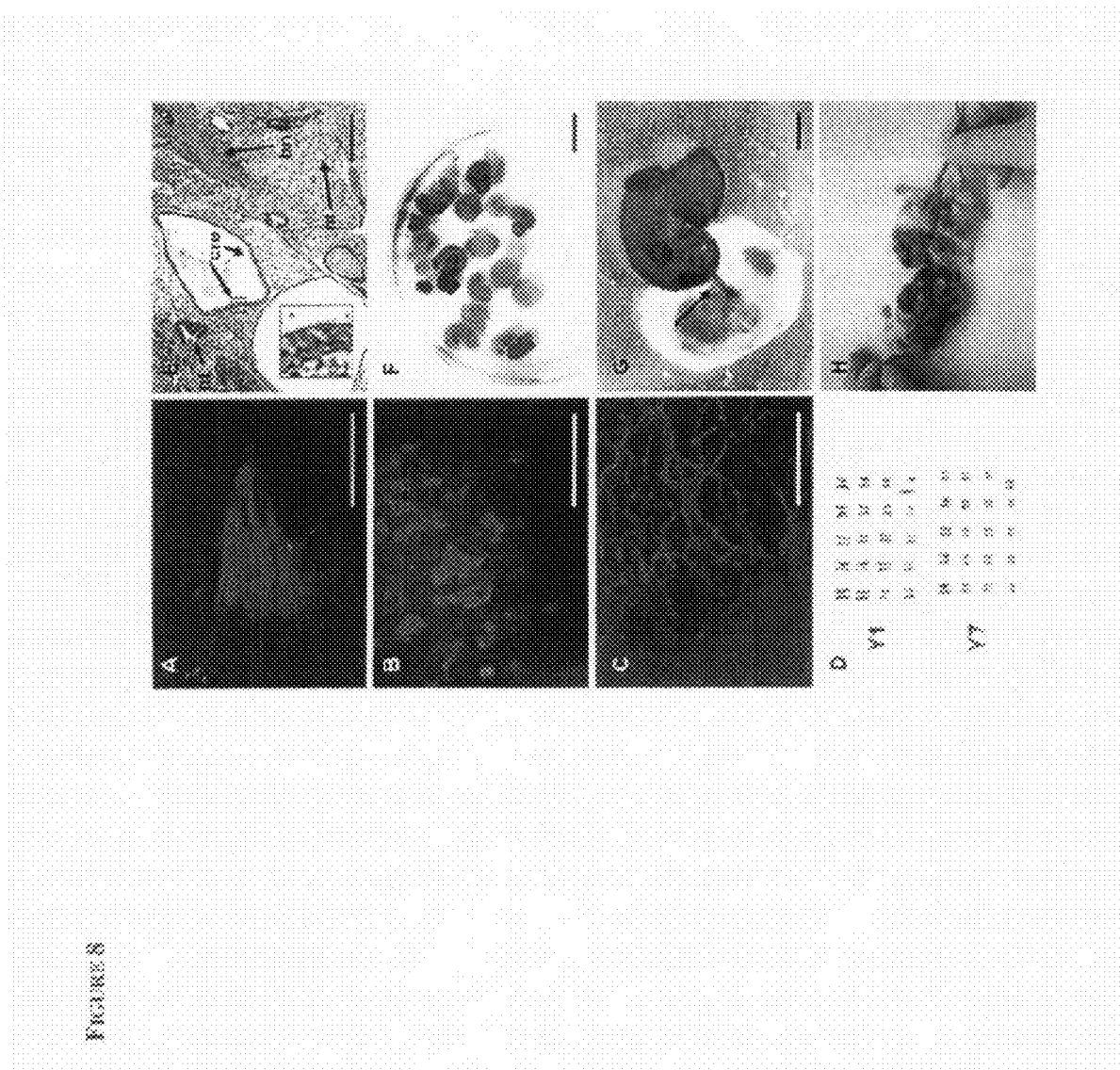
FIG. 8 depicts differentiation of blastomere-derived mES cells in vitro and in vivo.
Figure 9:
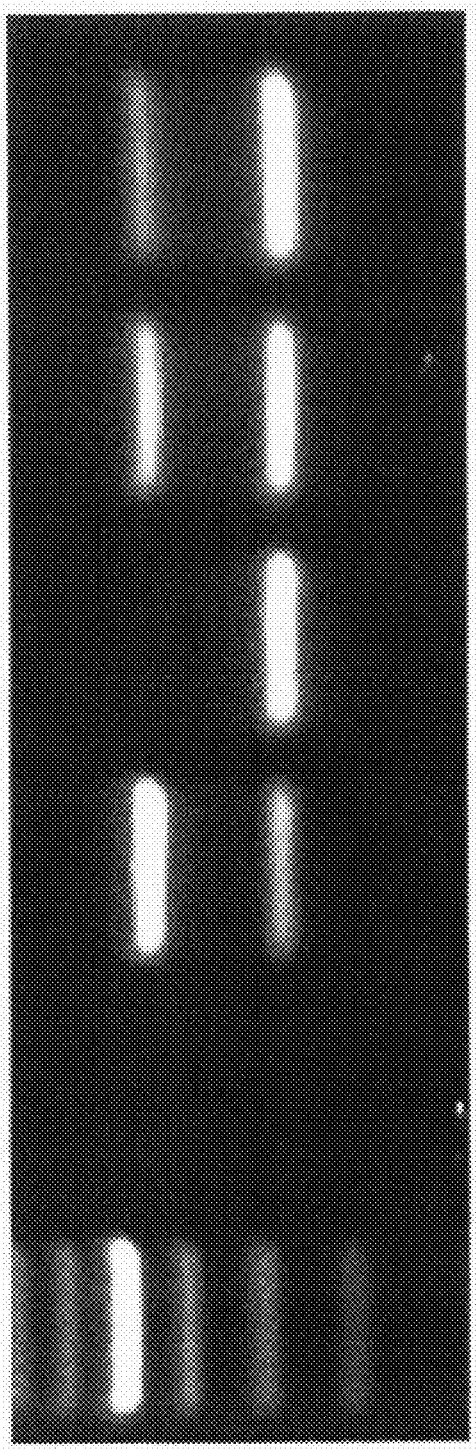
FIG. 9 shows PCR analysis demonstrating the presence of the LacZ gene in purified sperm from chimeric mice produced from two different blastomere-derived ES cell lines. The abbreviations present in FIG. 9 are to be understood as follows: M, molecular weight marker; H, $H_2O$ control; ES, DNA from mouse ES cells used to generate chimeric animals; CD-1, DNA from CD-1 mouse; SP-1, DNA from sperm of chimeric mouse No. 1; SP-2, DNA from sperm of chimeric mouse No. 2.

When the ES-like cell cultures were allowed to overgrow, they spontaneously differentiated into cells of all three germ layers, as evidenced by immunostaining with antibodies to muscle actin (mesoderm), βIII tubulin (ectoderm), and α-feto protein (primitive endoderm)(FIG. 3 B-D and FIG. 8 A-C). Beating heart muscle, extraembryonic endoderm and multiple neuronal cell types were also routinely observed in differentiating cultures. To further demonstrate the pluripotency of the derived ES cells, ES cell lines were either injected into CD-1 mouse blastocysts or aggregated with 8-cell stage morulae as described previously (Hogan et al., supra) and transferred to recipient females. X-Gal (5-bromo—4-chloro—3-indolyl-beta-D-galactopyranoside) staining of the resulting chimeric fetuses showed that the ES cell lines contributed to all organs (FIG. 3 A), such as, heart, kidney, liver, lung, intestine, brain, blood, skin and genital ridge. Twenty-four of the fetuses (83%) were chimeric (FIG. 8 F, G), and eight of nine (89%) pups (FIG. 8H) were chimeric; (the latter had the LacZ gene in their gametes (confirmed by PCR analysis; FIG. 9), and produced LacZ+ offspring when crossed with CD-1, confirming the contribution of the blastomere-derived ES cells to the germ line.).

To further analyze the pluripotency of the ES cells, the ES cells were injected into NOD-SCID mice and examined for their ability to differentiate into various cell types. Briefly, approximately 1 million ES cells were injected into the rear thigh of a NOD-SCID mouse. After about two months the mice were sacrificed and the teratomas excised, fixed in 4% paraformaldehyde, embedded in paraffin, and sectioned. The teratomas contained tissues from all three germ layers including bone and cartilage (mesoderm), neural rosettes (ectoderm), and ciliated respiratory epithelia (endoderm) among others (FIG. 8E).

| Exp. No. | No. blastomeres | No. non-GFP outgrowths detected after plating on MEF | No. non-GFP outgrowths passage 1 | ES lines established | Markers | | | | Differentiation | | | No chimeras/ fetuses | Karyotype |
|---|---|---|---|---|---|---|---|---|---|---|---|---|---|
| | | | | | Oct-4 | AP | Nanog | SSEA1 | In vitro Tb | AFP | muscle actin | | |
| 1 | 22 | 14 | 6 | 0 | | | | | | | | | |
| 2 | 24 | 13 | 8 | 0 | | | | | | | | | |
| 3 | 24 | 13 | 6 | J15 | + | + | + | + | + | + | + | 7/9 | 40XY |
| 4 | 21 | 16 | 5 | Y1 | + | + | + | + | + | + | + | 5/5 | 40XY |
| 5 | 15 | 8 | 5 | Y7 | + | + | + | + | + | + | + | 8/9 | 40XX |
| 6 | 19 | 11 | 6 | J5 | + | + | + | + | + | + | + | 4/6 | 60XXY |
| 6 | — | — | — | Y8 | + | + | + | + | + | + | + | — | 40XX |

The blastomere-biopsied embryos developed to term without a reduction in their developmental capacity (49% [23/47] live young versus 51% [38/75] for control non-biopsied embryos (Chi-square test, p=0.85). These results are consistent with human data, which indicates that normal and PGD-biopsied embryos develop into blastocysts with comparable efficiency. Although only 25 of 91 blastomeres (27%) generated inner cell mass (ICM)-like outgrowth, and only a few stable ES stem-cell lines were obtained in this study, we believe this success rate can be considerably increased by greater attention to the earliest stages of blastomere outgrowth, as well as the use of various measures which inhibit or influence the spontaneous differentiation of pluripotent cells into trophectoderm and other cell types.

These data show that ES cell lines can be derived without embryo destruction.

EXAMPLE 3

Generation of TS Cell Lines

Figure 5:
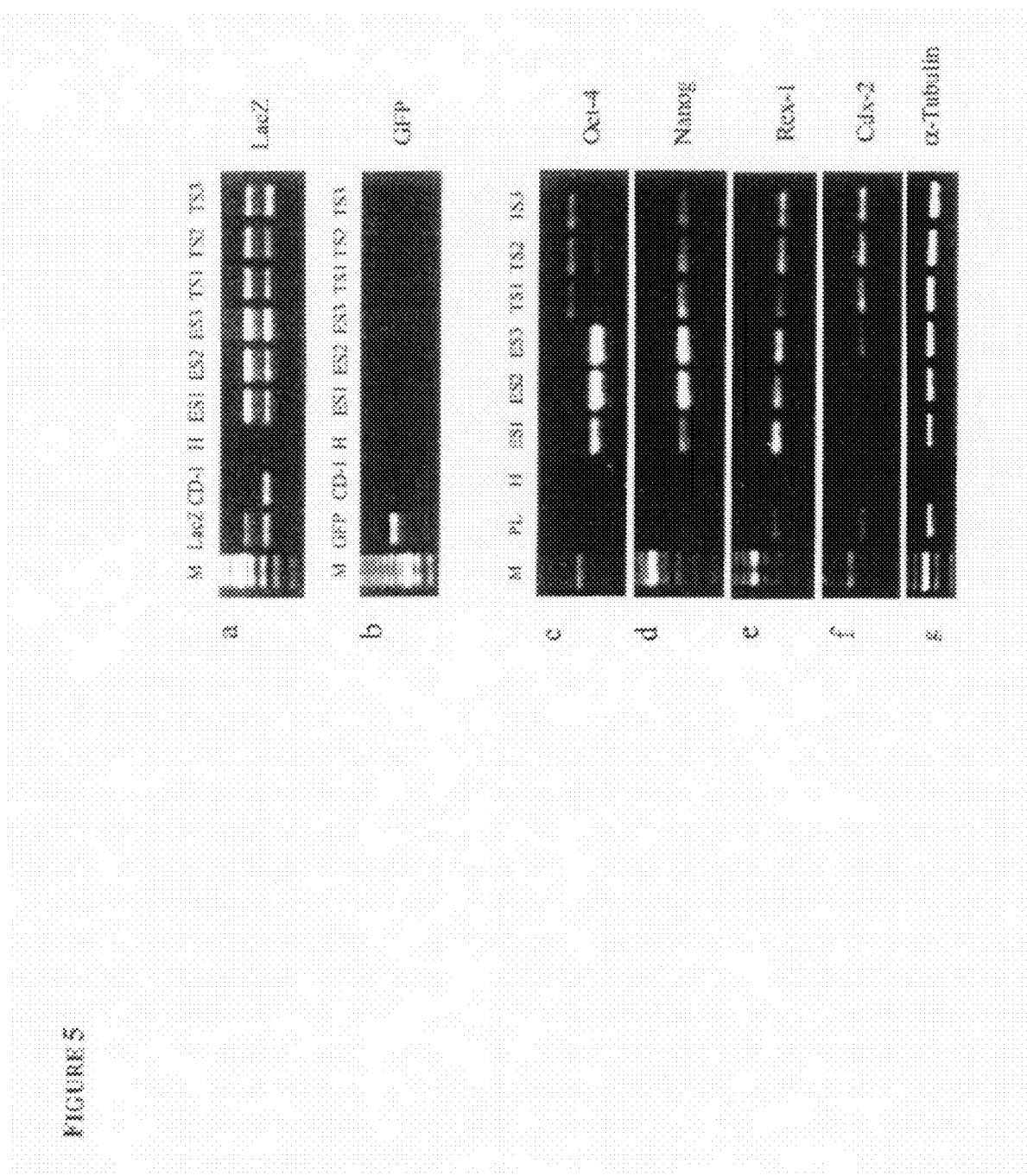
FIG. 5 shows PCR analysis of LacZ, GFP, and stem cell marker genes in embryonic stem and trophoblast stem ("TS") cell lines.
Figure 7:
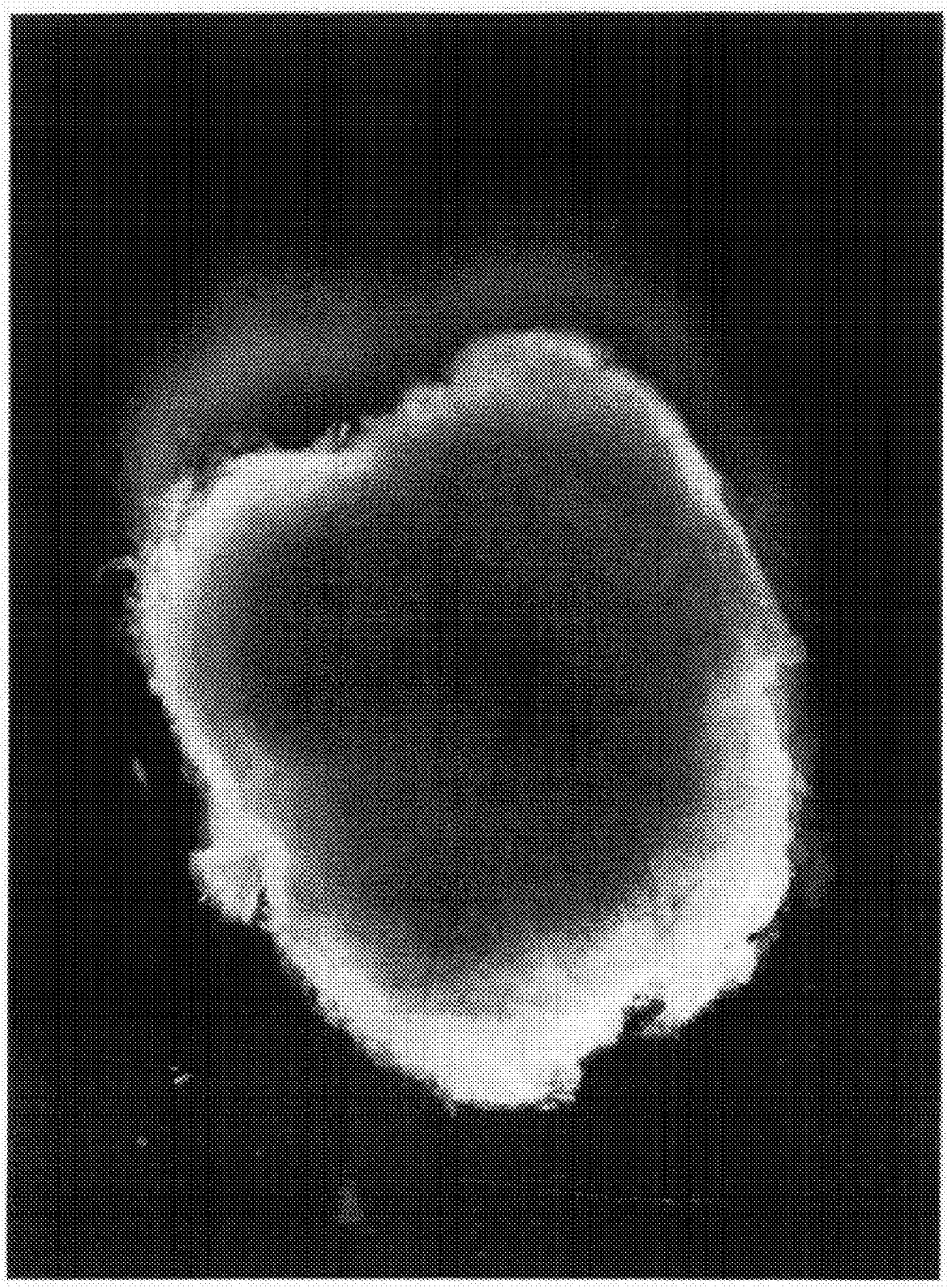
FIG. 7 shows LacZ stained placenta of 10.5 day chimera showing contribution of single blastomere-derived TS cells. The maternal portion of the placenta has been peeled away. In this figure, the embryonic portion shown is photographed from the distal side of the disk and is approximately 4 mm in diameter.

Blastomere outgrowths that morphologically resembled trophoblast and extraembryonic endoderm but not ES cells were further cultured in the mES cell medium with 50 ng/ml FGF-4 produced trophoblast stem (TS)-like cells that were maintained under these conditions and passaged with trypsin. Seven putative TS lines were established, which maintained normal karyotype and expressed markers of TS cells (FIG. 6 B, D, F, H, J). These cells were negative for Oct-4 (FIG. 6 H) and for α-feto protein. Putative TS cells contributed to the extraembryonic lineage in chimeric fetuses generated by aggregation with the LacZ$^+$ TS-cells (FIG. 7). RT-PCR analysis confirmed that these cells expressed Cdx-2, but not Oct-4 (FIG. 5 C and F). Nanog and Rex-1 were expressed in both the putative TS and ES cell lines (FIG. 5 D and E).

Briefly, RT-PCR analysis was performed as follows: Total RNA was isolated from ES and TS cells using an RNAeasy Mini Kit (Qiagen), and 1 µg RNA was subjected to first strand cDNA synthesis with an oligo (dT) primer, using AMV reverse transcriptase (Promega, Madison, Wis.). One tenth of the RT reaction was subjected to PCR amplification. PCR conditions for all genes were 95° C. for 9 min (1 cycle), 94° C. for 45 s, 62° C. for 1 min and 72° C. for 1.5 min with 2 mM Mg++ concentration, except for α-tubulin gene that was annealed at 64° C. Primers used were: Oct-4 gene, forward 5'-CTGAGGGCCAGGCAGGAGCACGAG-3' (SEQ ID NO:3), reverse 5'-CTGTAGGGAGGGCTTCGGGCACTT-3' (484 bp) (SEQ ID NO:4); Nanog gene, forward 5'-GGGTCTGCTACTGAGATGCTCTG-3' (SEQ ID NO:5), reverse 5'-CAACCACTGGTTTTTCTGCCACCG-3 (363 bp) (SEQ ID NO:6); Cdx2 gene, forward 5'-GGCGAAAC-CTGTGCGAGTGGATGCGGAA-3' (SEQ ID NO:7), reverse 5'-GATTGCTGTGCCGCCGCCGCTTCAGACC-3 (492 bp) (SEQ ID NO:8); Rex-1 gene, forward 5'-AGCAA-GACGAGGCAAGGCCAGTCCAGAATA-3' (SEQ ID NO:9), reverse 5'-GAGGACACTCCAGCATCGATAAGA-CACCAC-3' (423 bp) (SEQ ID NO: 10) and α-tubulin gene, forward 5'-CACCCGTCTTCAGGGCTTCTTGGTTT-3' (SEQ ID NO: 11), reverse 5'-CATTTCACCATCTGGTTG-GCTGGCTC-3'(527bp) (SEQ ID NO: 12). PCR products were separated on 1.5% agarose gel and visualized by ethidium bromide staining.

We claim:

1. An in vitro method of producing a culture of non-human mammalian embryonic stem (ES) cells, comprising: (a) obtaining a blastomere from a non-human mammalian embryo; (b) culturing said blastomere with ES or embryonic carcinoma (EC) cells to form ES cell colonies containing ES cell originating from said blastomere; and (c) isolating and culturing the ES cells originating from said blastomere.

2. The method of claim 1, wherein the blastomere is obtained from an embryo prior to compaction of the morula.

3. The method of claim 1, wherein the blastomere is obtained from an embryo during compaction of the morula.

4. The method of claim 1, wherein the blastomere is obtained by partially or completely removing the zona pellucida surrounding the embryo.

5. The method of claim 1, wherein the blastomere is cultured with embryo carcinoma cells.

6. The method of claim 1, wherein the blastomere is cultured with ES cells.

7. The method of claim 1, wherein the blastomere is cultured with factors that inhibit differentiation of ES cells.

8. The method of claim 1, wherein recombinant Oct-4 is introduced into the blastomere.

9. The method of claim 1, wherein the ES cells of step (c) express an ES cell marker protein.

10. The method of claim 1, wherein the blastomere undergoes cell division and one progeny cell is used for genetic testing and a different progeny cell is used to produce an ES cell.

11. A method of producing a non-human mammalian embryonic stem (ES) cells, comprising the steps of: (a) obtaining a blastomere from a non-human mammalian embryo; (b) aggregating the blastomere with ES cells; (c) culturing the aggregated blastomere and ES cells until ES cells derived from the blastomere form; and (d) isolating the ES cells derived from the blastomere.

12. A method of producing an ES cell line comprising the step of culturing the ES cells produced by the method of claim 1, to produce an ES cell line.

13. The method of claim 11, wherein the blastomere is obtained from an embryo prior to compaction of the morula.

14. The method of claim 11, wherein the blastomere is obtained from an embryo during compaction of the morula.

15. The method of claim 11, wherein the blastomere is obtained by partially or completely removing the zona pellucida surrounding the embryo.

16. The method of claim 11, wherein the blastomere is cultured with factors that inhibit differentiation of the ES cells.

17. The method of claim 11, wherein recombinant Oct-4 is introduced into the blastomere.

18. The method of claim 11, wherein at least one ES cell derived from the blastomere expresses an ES cell marker protein.

19. The method of claim 11, wherein at least one ES cell derived from the blastomere is used for genetic testing.

20. The method of claim 11, wherein the embryo is cryopreserved after step (a).

21. The method of claim 20, wherein the embryo is cultured before being cryopreserved.

22. The method of claim 1, wherein the embryo is cryopreserved after step (a).

23. The method of claim 22, wherein the embryo is cultured before being cryopreserved.

24. A method of producing an ES cell line comprising the step of culturing the ES cells produced by the method of claim 11 to produce an ES cell line.

25. A method of producing a culture of non-human mammalian embryonic stem (ES) cells, comprising the steps of: (a) isolating a blastomere from an 8-cell stage embryo by biopsy through a hole drilled in the zona pellucida or by zona-denuding and disaggregating said embryo; (b) culturing said blastomere with ES cells to form clumps of cells that comprise ES cells originated from said blastomere; and (c) isolating and dissociating said clumps of cells, and further isolating and culturing the ES cells that originated from said blastomere to produce a cell culture of ES cells that originated from said blastomere.

* * * * *

SEQUENCE LISTING

<160> NUMBER OF SEQ ID NOS: 12

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ttgaattcgc caccatggtg agc                                          23

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ttgaattctt acttgtacag ctcgtcc                                      27

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      primer -continued

```
<400> SEQUENCE: 3
ctgagggcca ggcaggagca cgag                                           24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ctgtagggag ggcttcgggc actt                                           24

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gggtctgcta ctgagatgct ctg                                            23

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
caaccactgg tttttctgcc accg                                           24

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggcgaaacct gtgcgagtgg atgcggaa                                       28

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gattgctgtg ccgccgccgc ttcagacc                                       28

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 9
agcaagacga ggcaaggcca gtccagaata                                    30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gaggacactc cagcatcgat aagacaccac                                    30

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cacccgtctt cagggcttct tggttt                                        26

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
catttcacca tctggttggc tggctc                                        26
```